(12) United States Patent
Kim et al.

(10) Patent No.: US 9,308,253 B2
(45) Date of Patent: Apr. 12, 2016

(54) CANCER IMMUNOTHERAPY

(71) Applicant: The Johns Hopkins University, Baltimore, MD (US)

(72) Inventors: Young Jun Kim, Ellicot City, MD (US); Drew M. Pardoll, Brookville, MD (US); Juan Fu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 6 days.

(21) Appl. No.: 14/345,588

(22) PCT Filed: Sep. 19, 2012

(86) PCT No.: PCT/US2012/055992
§ 371 (c)(1),
(2) Date: Mar. 18, 2014

(87) PCT Pub. No.: WO2013/043647
PCT Pub. Date: Mar. 28, 2013

(65) Prior Publication Data
US 2014/0341978 A1    Nov. 20, 2014

Related U.S. Application Data

(60) Provisional application No. 61/536,115, filed on Sep. 19, 2011.

(51) Int. Cl.
*A61K 39/395*  (2006.01)
*A61K 39/39*   (2006.01)
*A61K 45/06*   (2006.01)
*A61K 35/13*   (2015.01)
*A61K 39/00*   (2006.01)
*C07K 16/28*   (2006.01)

(52) U.S. Cl.
CPC .............. *A61K 39/39* (2013.01); *A61K 35/13* (2013.01); *A61K 39/0011* (2013.01); *A61K 39/395* (2013.01); *A61K 45/06* (2013.01); *C07K 16/2818* (2013.01); *A61K 2039/5152* (2013.01); *A61K 2039/55516* (2013.01)

(58) Field of Classification Search
CPC .............. A61K 39/0011; A61K 2039/5152; A61K 48/00; A61K 2039/55522; A61K 39/39558; A61K 2039/57
See application file for complete search history.

(56) References Cited

U.S. PATENT DOCUMENTS

| 2005/0002916 A1* | 1/2005 | Jooss et al. ............... 424/93.21 |
| 2008/0145375 A1 | 6/2008 | Bembridge et al. |
| 2009/0028857 A1* | 1/2009 | Li et al. ..................... 424/133.1 |
| 2009/0081157 A1 | 3/2009 | Kornbluth et al. |
| 2010/0086550 A1 | 4/2010 | Kang et al. |
| 2010/0291192 A1* | 11/2010 | Haensler et al. ............. 424/450 |
| 2011/0159081 A1* | 6/2011 | Biemans et al. ............. 424/450 |

FOREIGN PATENT DOCUMENTS

| WO | 2010024897 A2 | 3/2010 |
| WO | 2011136828 A1 | 11/2011 |

OTHER PUBLICATIONS

Chiang et al, "Whole tumor antigen vaccines" Seminars in Immunology, 2010, vol. 22, No. 3, pp. 132-143.
Davies et al. "Intratumoral administration of TLR4 agonist absorbed into a cellular vector improves anti-tumor responses" Clin.Cancer Res.,Jun. 15, 2011, vol. 17, No. 12, pp. 3984-3992.
International Search Report and Written Opinion mailed Feb. 25, 2013, for PCT/US2012/055992.
Extended European Search Report issued in related European Application No. 12834327.4, dated Feb. 11, 2015.
Li et al., "Anti-Programmed Death-1 Synergizes with Granulocyte Macrophage Colony-Stimulating Factor-Secreting Tumor Cell Immunotherapy Providing Therapeutic Benefit to Mice with Established Tumors," Clinical Cancer Research, vol. 15, No. 5, Mar. 1, 2009, pp. 1623-1634.
Curran et al., "PD-1 and CTLA-4 combination blockade expands infiltrating T cells and reduces regulatory T and myeloid cells within B16 melanoma tumors," Proceedings of the National Academy of Sciences, vol. 107, No. 9, Mar. 2, 2010, pp. 4275-4280.
Fu et al., "Preclinical Evidence That PD1 Blockade Cooperates with Cancer Vaccine TEGVAX to Elicit Regression of Established Tumors," Cancer Research, vol. 74, No. 15, May 8, 2014, pp. 4042-4052.

\* cited by examiner

*Primary Examiner* — Daniel C Gamett
(74) *Attorney, Agent, or Firm* — Banner & Witcoff, LTD

(57) ABSTRACT

We formulated multiple TLR agonists into GVAX (lethally irradiated tumor cell vaccines engineered to secrete GM-CSF). Specifically, GLA and R848, TLR4 and TLR7/8 agonists found to be safe in patients, were formulated with GVAX (TEGVAX—for TLR agonists enhanced GVAX), and this formulation was effective in producing anti-tumor responses in 3 different preclinical models, including palpable B16. These anti-tumor responses were correlated with increased CD4 and CD8 T-cells that can secrete IFNγ circulating in the tumor microenvironment as well as significantly higher level of p15E specific CTL mediated cell killing in mice treated with TEGVAX in comparison to controls. When combined with anti-PD-1 antibody, TEGVAX was able to induce regression of established B16 tumors.

27 Claims, 12 Drawing Sheets

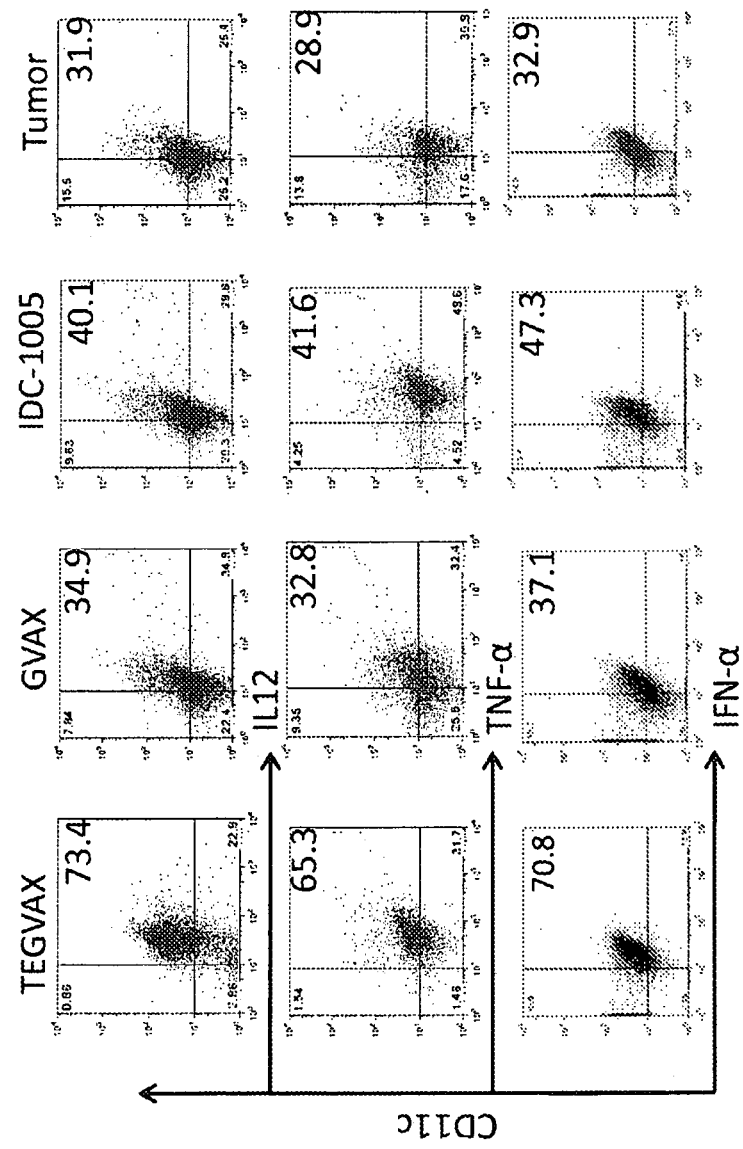
Figure 8 (Supplemental Figure 1)

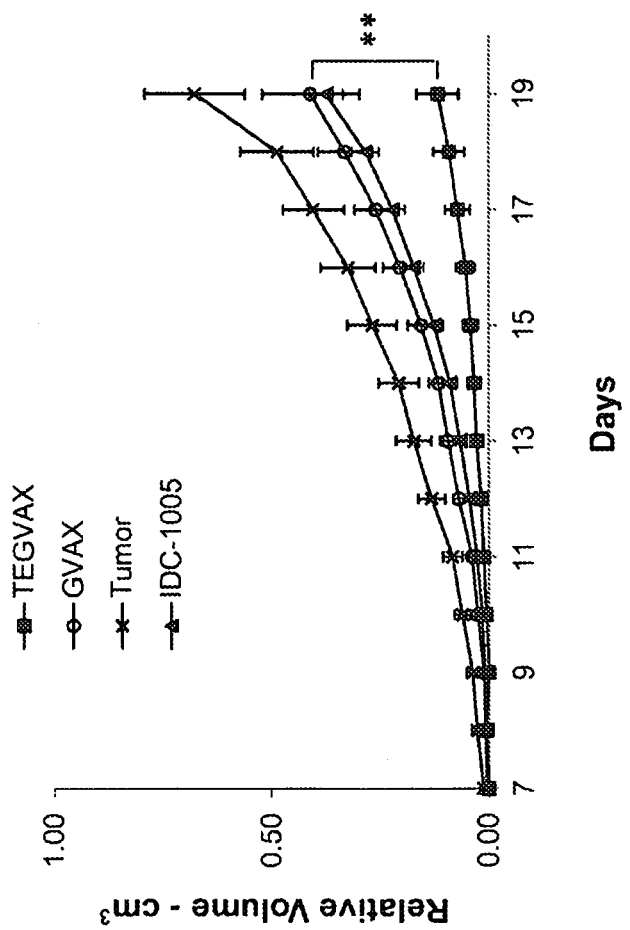
Figure 9 (Supplemental Figure 2)

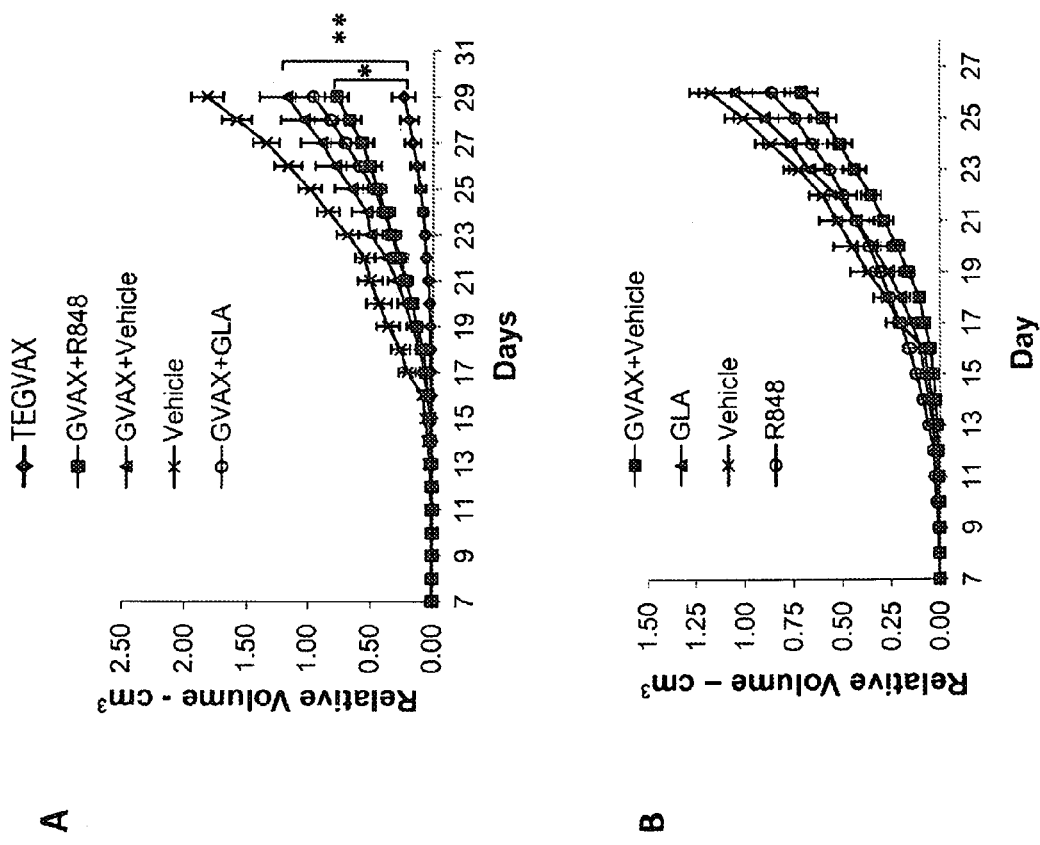
Figure 10 (Supplemental Figure 3)

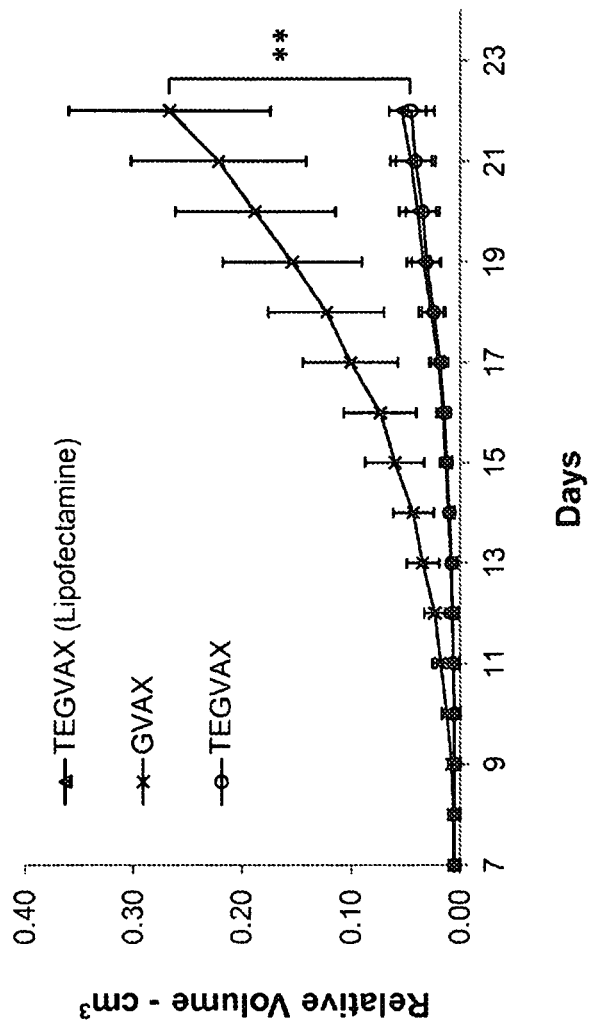
Figure 11 (Supplemental Figure 4)

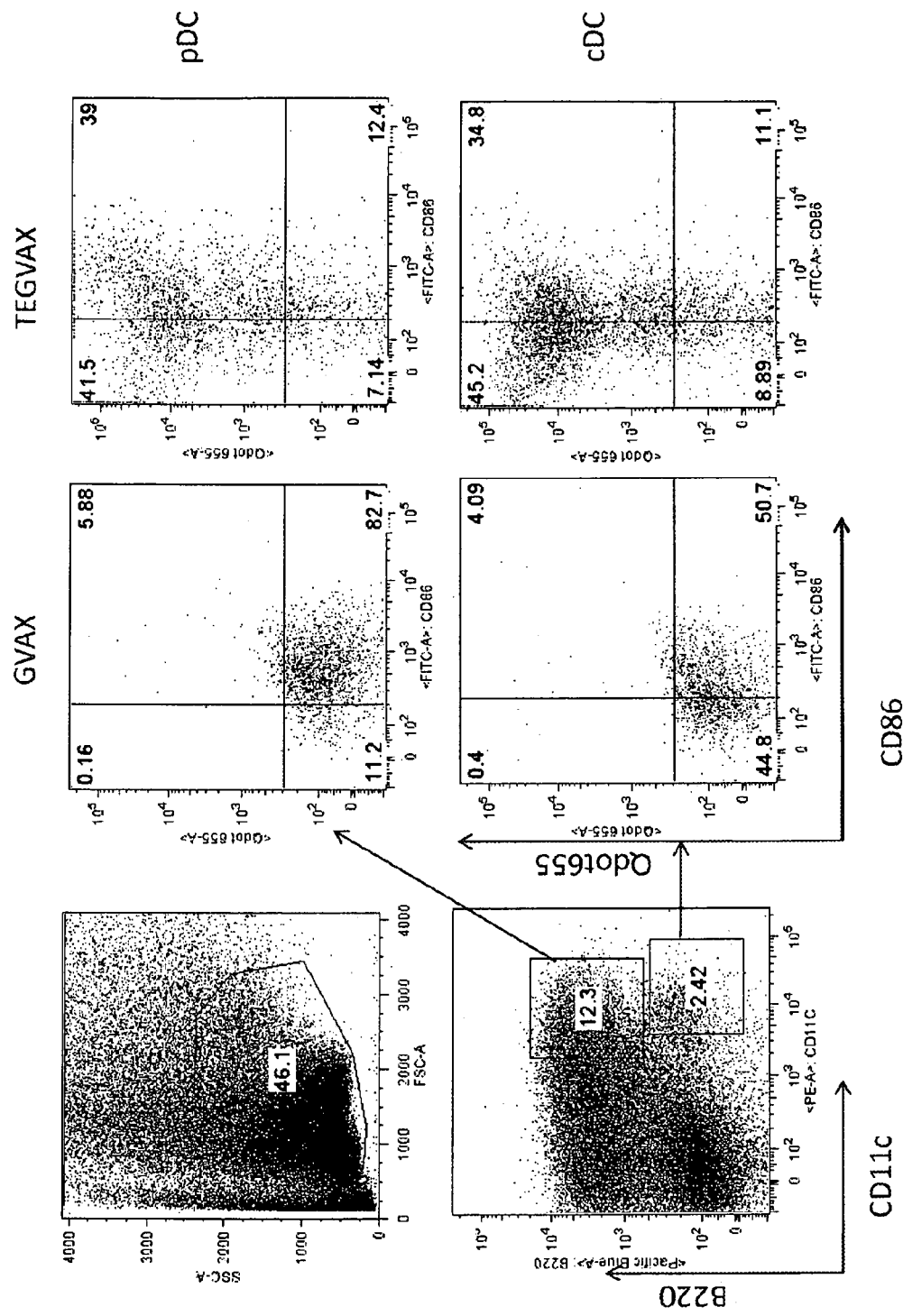
Figure 12 (Supplemental Figure 5)

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: P15E peptide

<400> SEQUENCE: 1

Lys Ser Pro Trp Phe Thr Thr Leu
 1               5

<210> SEQ ID NO 2
<211> LENGTH: 9
<212> TYPE: PRT
<213> ORGANISM: Artificial Sequence
<220> FEATURE:
<223> OTHER INFORMATION: beta-gal peptide

<400> SEQUENCE: 2

Thr Pro His Pro Ala Arg Ile Gly Leu
 1               5

CANCER IMMUNOTHERAPY

This invention was made with support from the National Institutes of Health. Therefore the U.S. government retains certain rights under the terms of grant no. NIH K23-DE018464-02.

TECHNICAL FIELD OF THE INVENTION

This invention is related to the area of cancer therapy. In particular, it relates to cancer immunotherapy.

BACKGROUND OF THE INVENTION

Due to its extensive history of safety as well as availability in multiple tumor types, lethally irradiated tumor cell vaccines engineered to secrete GM-CSF (GVAX) is one vaccine platform that has potential for combinatorial therapy with immune checkpoint blockade antibodies. However, local GM-CSF secreted by GVAX can mobilize myeloid precursors into macrophages and dendritic cells, but this cytokine may not induce their activation. Thus, a major limitation of GVAX is in the activation of antigen presenting cells (APC) necessary for optimal tumor antigen presentation in the afferent arm of the immune system. One simple strategy that phenocopies the robust immunological responses seen in vaccines against infectious agents is to combine multiple TLR agonists with a cancer cell-based vaccine. Clinically, multiple adjuvants have been developed for cancer patients to augment the potency of cancer vaccines, and many of these adjuvants are typically TLR agonists.

One real concern with non-targeted TLR stimulation is the procarcinogenic consequences of chronic TLR stimulation in the tumor cells. Stimulation of TLR4 receptors expressed on tumor cells has shown to promote carcinogenesis. TLR signaling in the hematopoietic compartment, however, has been shown to elicit anti-tumor responses, which have translated into multiple clinical trials. In order to target the dendritic cells in the tumor microenvironment and test whether TLR4 stimulation in the tumor microenvironment can induce a procarcinogenic effect in vivo, our group injected LPS formulated GVAX intratumorally and found that intratumoral injection of TLR4 ligand absorbed GVAX improved the local anti-tumor response in vivo in three different murine models.

There is a continuing need in the art to obtain safer and more effective treatments of tumors.

SUMMARY OF THE INVENTION

According to one aspect of the invention a composition is provided which may be used for treating cancer patients. The composition comprises (a) cytokine expressing, proliferation incompetent, whole cancer cells; (b) an anti-PD-1 antibody that specifically binds to human Programmed Death 1 (PD-1); and (c) a TLR (toll like receptor) agonist; wherein the whole cancer cells are formulated with the TLR agonist.

According to another aspect of the invention a method is provided. Agents are administered to a cancer patient. The agents are: (a) cytokine-expressing, proliferation incompetent, whole cancer cells; (b) an anti-PD-1 antibody that specifically binds to human Programmed Death 1 (PD-1); and (c) a TLR (toll like receptor) agonist; wherein the whole cancer cells are formulated with the TLR agonist. The whole cancer cells are formulated with the TLR agonist.

According to another aspect of the invention a kit is provided which comprises the agents: (a) cytokine-expressing, proliferation incompetent, whole cancer cells; (b) an anti-PD-1 antibody that specifically binds to human Programmed Death 1 (PD-1); and (c) a TLR (toll like receptor) agonist; wherein the whole cancer cells are formulated with the TLR agonist. Optionally the whole cancer cells are formulated with the TLR agonist.

These and other embodiments which will be apparent to those of skill in the art upon reading the specification provide the art with

BRIEF DESCRIPTION OF THE DRAWINGS

FIG. 1A. From day 3 after vaccine injection in non-tumor bearing mice, pDC and cDC gated populations from vaccine draining LN were quantitated for CD86. IDC-1005 is GLA and R848 in 10% (w/v) squalene oil-in-water vehicle and TEGVAX is IDC-1005 formulated with irradiated GVAX. FIG. 1B. TEGVAX induced increased CD86 and CD80 activation markers on the pDC from the draining lymph nodes in comparison to GVAX day 3 after vaccine injection ($*P<0.05$). FIG. 1C. TEGVAX has increased CD86 and CD80 activation markers on the cDC from the draining lymph nodes in comparison to GVAX day 3 after vaccine injection ($*P<0.05$). FIG. 1D. CD86+ pDC and cDC from DLN from day 3 to 7 after injection with TEGVAX or GVAX.

FIG. 2A. Mice with palpable B16 melanoma were treated with GVAX, TEGVAX (GVAX/IDC-1005), and IDC-1005 in the contralateral limb and the volume of tumor measured daily. IDC-1005 is GLA and R848 in 10% (w/v) squalene oil-in-water emulsion. FIG. 2B. Palpable B16 melanomas treated with multiple injections of vaccines and TLR agonists on day7, day14 and day28 (arrow). FIG. 2C. Palpable SCCFVII tongue cancer was treated with $10^6$ SCCFVII-GVAX in the contralateral limb and the tumor was measured daily. C3H/HeOUJ mice treated With TEGVAX regressed, and these mice were rechallenged with SCCFVII $5\times10^4$ and $1\times10^5$ on day22 and day27, respectively at a different site (arrowhead) ($*P<0.05$; $**P<0.01$). No tumor grew at these rechallenge sites. FIG. 2D. B16 treatment assay were performed with TEGVAX (1 hour incubation of GVAX and IDC-1005) vs. GVAX and IDC-1005 mixture without incubation. The incubation group had significantly anti-tumor effect in comparison to the no incubation group ($*P<0.05$).

FIG. 3A. B16 tumor tissue from each of the treatment groups were harvested and stained with H&E. TEGVAX treated tumor showed increased number of necrotic foci (circled areas, 20×). FIG. 3B. Necrotic foci were quantified in 10 separate regions under 20× magnification in tumor tissue treated with TEGVAX and GVAX ($**P<0.01$). FIG. 3C. Frozen tumor tissue was stained with αCD4 and αCD8 FITC conjugates and counterstained with DAPI in each of the treated groups. TEGVAX treated B16 melanoma had increased infiltration of CD4 and CD8 cells in the tumor microenvironment tumor tissue. FIG. 3D. The tumor infiltrating CD4, CD8, and CD86 cells were randomly counted in 10 different fields with immunofluorescent microscope. TEGVAX treated. B16 tumors had significantly increased infiltrating lymphocytes in comparison to GVAX and IDC-1005 treated tumors ($*P<0.05$; $**P<0.01$).

FIG. 4A. Tumor draining lymph nodes were harvested from the treated mice and intracellular staining of IFNγ from both CD4 and CD8 populations were performed. FIG. 4B. Mean fluorescent intensity of CD4+ IFNγ+ and CD8+ IFNγ+ were quantitated in each of the treated groups. FIG. 4C. Treated tumor tissue were harvested and stained with rat anti-mouse B7-H1 antibodies and anti-rat Cy3 conjugate were used to assess B7-H1 positive cells. Blinded quantitation was performed in 10 different fields at 40× magnification and is summarized in FIG. 4D.

FIG. 5A. Both GK1.5 (CD4 depleting) and 2.43 (CD8 depleting) antibodies were injected intraperitoneally during the vaccine treatment. FIG. 5B. CD4, CD8 cells were depleted individually in the TEGVAX and control treatment assay. FIG. 5C. The anti-tumor response of TEGVAX is abrogated in Rag2−/− mice. FIG. 5D. The anti-tumor response of TEGVAX is abrogated in MyD88−/− and TRIF−/− double knockout mice. The in viva effect of TEGVAX is identical to GVAX in these TLR signaling defective mice (**P<0.01).

FIG. 6A. In viva CTL assay was performed on day 25 after vaccine treatment from each of the treated groups. P15E peptide-specific killing was calculated using the following formula: $(1-\% \text{ of } CFSE_{peptide}/\% \text{ of } CFSE_{no\ peptide}) \times 100$. FIG. 6B. ELISPOT assay on splenocytes from each of the treated groups on day 23. P15E peptide was pulsed into T2kb APC (**P<0.01).

FIG. 7A. Right panel shows tumor growth rate of established B16 tumor treated with various combinations of vaccines and anti-PD-1. FIG. 7B. Left panel shows two mice—right mice is one of the mice treated with TEGVAX/anti-PD-1, left mice is one of the mice treated with GVAX. TEGVAX treated mice did not show any regression. Circles show the site of tumor inoculation. Arrow shows the site of vitiligo. FIG. 7C. Tumor draining lymph nodes were harvested and TH1cytokines were quantitated from CD4, CD8, and CD11c+ DC cells.

FIG. 8 (Supplemental FIG. 1). Increased IL-12, TNF-α, and IFN-α in tumor draining LN of TEGVAX treated mice. Tumor DLN were harvested and Th1 cytokine profiles on CD11c+ cells were analyzed in each of the treated groups. TEGVAX treated mice had significantly increased IL12, TNF-α and IFN-α positive CD11c+ cells in comparison to GVAX or the control treated groups.

FIG. 9 (Supplemental FIG. 2.) TEGVAX induces anti-tumor response in established CT26 model. $10^5$ CT26 colon cancer cells were injected into the footpad, and mice with palpable tumors were treated with the vaccines. CT26-GVAX were prepared as described in Yoshimura et. al. (11). TEGVAX significantly decreased mice CT26 colon cancer growth in comparison to CT26-GVAX alone or with IDC-1005 alone (**P<0.01).

FIG. 10A-B (Supplemental FIG. 3.) Multiple TLR agonists formulated into TEGVAX had the greatest anti-tumor response in vivo. FIG. 10A. Mice bearing palpable B16 tumor was treated with TEGVAX, GVAX, GVAX formulated with R848, or GVAX formulated with GLA. All formulation consisted of incubating B16-GVAX with adjuvants in 1.0% (w/v) squalene oil-in-water emulsion vehicle for 1 hr at 4 deg C. prior to vaccine injection (**P<0.01). FIG. 10B. Individual, adjuvants with vehicle without GVAX had no in vivo anti-tumor effects.

FIG. 11 (Supplemental FIG. 4). TEGVAX formulated with absorbed GLA and R848 using Lipofectamine™ 2000 (Invitrogen) had comparable in vivo anti-tumor effect as TEGVAX formulated with oil-in-water emulsion vehicle (**P<0.01).

FIG. 12. (Supplemental FIG. 5). TEGVAX increased the number of activated DC that have endogenously endocytosed Q-dot, a surrogate tumor antigen, from the vaccine. GVAX and TEGVAX were labeled with Qtracker 655 (Invitrogen) and inoculated into mice footpads. After 3 days the draining popliteal LNs were harvested, and lymphocytes depleted with CD3 and CD19 antibodies. FACS analysis quantified endogenous pDC and cDC labeled with Q-dot from the vaccines.

DETAILED DESCRIPTION OF THE INVENTION

Figure 1:
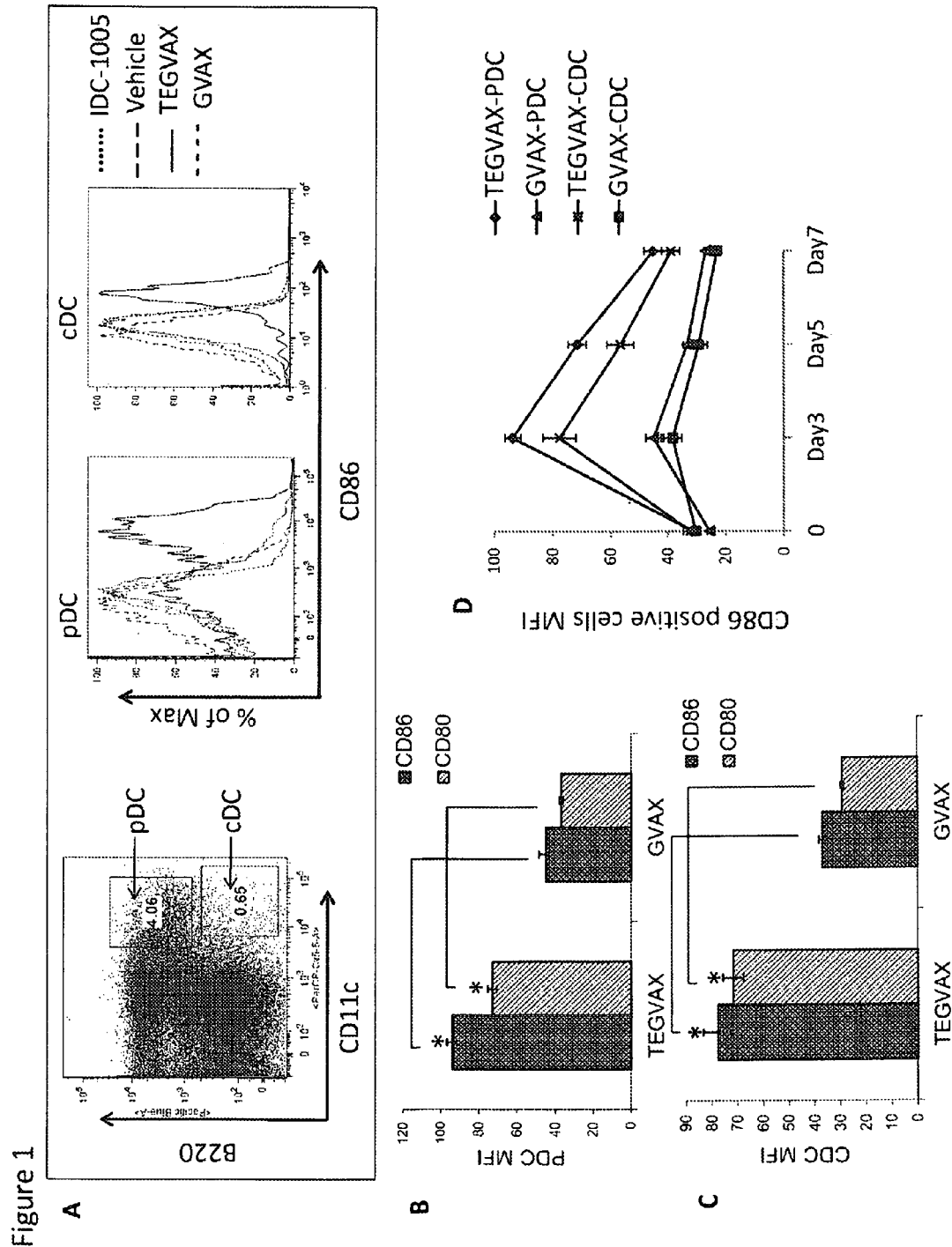
FIG. 1A-1D. TEGVAX can increase activated plasmacytoid (pDC) and conventional DC (cDC) in the draining lymph nodes.

We have developed in vivo evidence that optimally formulated cancer vaccines combined with PD-1 blockade can be used therapeutically for treating tumors. We have collected evidence demonstrating that the combination regimen can be effective against established tumors that are poorly immunogenic. All the components of this combinatorial regimen have been individually tested in patients and found to be clinically safe. The disclosed treatment strategy may work by adaptive immune evasion, although applicants do not intend to be bound by any proposed mechanism of action.

Patients having a variety of cancers may be treated with the combination regimen. Such cancers include colorectal cancer, an aero-digestive squamous cancer, a lung cancer, a brain cancer, a liver cancer, a stomach cancer, a sarcoma, a leukemia, a lymphoma, a multiple myeloma, head-and-neck cancer, an ovarian cancer cervical cancer, a uterine cancer, a breast cancer, a melanoma, a prostate cancer, a pancreatic carcinoma, and a renal carcinoma. This list is meant to be illustrative rather than limiting.

Whole cancer cells may be allogeneic, syngeneic, or autologous to the treatment recipient. Typically they may be treated to make them proliferation incompetent by a technique which preserves preserve their immunogenicity and their metabolic activity. One typically used technique is irradiation. Such cells. Typically the same general type of tumor cell is used that the patient bears. For example, a patient suffering from melanoma will typically be administered proliferation incompetent melanoma cells. The cells may express and secrete a cytokine naturally or by transfection with a nucleic acid which directs such expression and secretion. One suitable cytokine is GM-CSF. For example, the tumor cell may express a transgene encoding GM-CSF as described in U.S. Pat. Nos. 5,637,483, 5,904,920, 6,277,368 and 6,350,445, as well as in US Patent Publication No. 20100150946, each of which is expressly incorporated by reference. One example of a GM-CSF-expressing, genetically modified cancer cell for the treatment of pancreatic cancer is described in U.S. Pat. Nos. 6,033,674 and 5,985,290, both of which are expressly incorporated by reference herein. Other cytokines can be used. Suitable cytokines which may be used include cytokines which stimulate dendritic cell induction, recruitment, and/or maturation. Such cytokines include, but are not limited to, one or more of GM-CSF, CD40 ligand, IL-12, CCL3, CCL20, and CCL21. Granulocyte-macrophage colony stimulating factor (GM-CSF) polypeptide is a cytokine or fragment having immunomodulatory activity and having at least about 85% amino acid sequence identity to GenBank Accession No. AAA52122.1.

According to one alternative embodiment, cytokines are delivered by inactivated bystander cells which express and secrete one or more cytokines. The bystander cells may provide all of the cytokines which stimulate dendritic cell induction, recruitment, and/or maturation, or may supplement cytokines secreted by the inactivated tumor cells. Immunomodulatory cytokine-expressing bystander cell lines are described in U.S. Pat. Nos. 6,464,973, and 8,012,469, Dessureault et al., Ann. Surg. Oncol. 14: 869-84, 2007, and Eager and Nemunaitis, Mol. Ther. 12: 18-27, 2005, each of which is expressly incorporated by reference.

Antibodies which are suitable for use in the treatment regimen and compositions and kits include any which specifically bind to Programmed Death 1. (PD-1). Exemplary types of antibodies which may be employed include without limitation human, humanized, chimeric, monoclonal, polyclonal, single chain, antibody binding fragments, and diabodies. Typically antibodies are substantially encoded by an immunoglobulin gene or immunoglobulin genes, or fragments thereof. Antibodies are capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. An antibody typically specifically binds to an antigen or epitope. Specific binding occurs to the corresponding antigen or epitope even in the presence of a heterogeneous population of proteins and other biologics. Specific binding of an antibody indicates that it binds to its target antigen or epitope with an affinity that is substantially greater than binding to irrelevant antigens The relative difference in affinity is often at least 25% greater, more often at least 50% greater, most often at least 100%. The relative difference can be at least 2×, at least 5×, at least 10×, at least 25×, at least 50×, at least 100×, at least 1.000×, for example.

Toll like receptors (TLR) are a family of proteins that sense a microbial product and/or initiates an adaptive immune response. TLR activate a dendritic cell (DC). TLRs are conserved membrane spanning molecules containing an ectodomain of leucine-rich repeats, a transmembrane domain and an intracellular TIR. (Toll/IL-1R) domain. TLRs recognize distinct structures in microbes; often referred to as "PAMPs" (pathogen associated molecular patterns). Ligand binding to TLRs invokes a cascade of intra-cellular signaling pathways that induce the production of factors involved in inflammation and immunity.

Exemplary agonists which may be used for these receptors include, without limitation lipoproteins, lipopolypeptides, peptidoglycans, zymosan, lipopolysaccharide; neisserial porins, flagellin, profilin, galactoceramide, muramyl dipeptide, glucopyranosyl lipid A (GLA), and resiquimod (R848). Peptidoglycans, lipoproteins, and lipoteichoic acids are cell wall components of Gram-positive. Lipopolysaccharides are expressed by most bacteria. Flagellin is the structural component of bacterial flagella that is secreted by pathogenic and commensal bacterial. A Galactosylceramide (α-GalCer) is an activator of natural killer T (NKT) cells. Muramyl dipeptide is a bioactive peptidoglycan motif common to all bacteria. Such agonists mediate innate immune activation via Toll-like Receptors. Specific binding of an agonist for its cognate receptor is often expressed in terms of an affinity. The ligands of the present invention may bind with affinities of between about $10^4$ $M^{-1}$ and about $10^8$ $M^{-1}$. Affinity is calculated as $K_d = k_{off}/k_{on}$ ($k_{off}$ is the dissociation rate constant, $K_{on}$ is the association rate constant and $K_d$ is the equilibrium constant). Single or multiple agonists may be used.

In humans, ten TLR have been identified. TLRs that are expressed on the surface of cells include TLR-1, -2,-4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, WIC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and useful in the present invention include, but are not limited to, the following:
Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUCI mucin on a number of human cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Formulation of the whole cancer cells with the TLR agonist appears to be a contributing factor to enhanced efficacy. Formulations can be incubated together for periods of times such as ¼, ½, 1, 2, 3, 5, 10, 24 hours, at temperatures such as 4 degrees C. Alternatively, binding in the presence of a lipophilic agent or an emulsifying agent can be employed. Such agents are well known in the art.

Various dosing schedules may be envisioned, with simultaneous or staggered timing, with single or multiple agents, single cycle or multiple cycles.

Methods of administering treatment agents to cancer patients vary. Exemplary methods include without limitation subcutaneous, intravenous, intramuscular, intraarterial, intradermal, intrathecal, intratumoral, intraperitoneal, sublingual, and epidural administrations. Administration may be to a human, mammal, mammalian subject, animal, veterinary subject, placebo subject, research subject, or experimental subject. Typically an agent such as an exogenous ligand, reagent, placebo, small molecule, pharmaceutical agent, therapeutic agent, diagnostic agent, or composition is contacted with the subject in an appropriate anatomical location. Administration may be for the purposes of therapy, pharmacokinetic study, diagnostic assay, research, placebo, or experimental method. Agents according to the invention may be, but not need not be, administered as a single composition. Although administration as a single composition is contemplated by the present invention, agents may be delivered to a single subject as separate administrations, which may be at the same or different time, and which may be by the same route or different routes of administration. In some cases, the agents may in fact contact each other within the subject's body, forming a composition in vivo.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

In order to evaluate the capacity of multiple TLR agonists to induce systemic anti-tumor immunity in the clinical setting, we formulated glucopyranosyl lipid A (GLA-TLR4 agonist) and resiquimod (TLR7/8 agonist) with GVAX and studied their anti-tumor effects in vivo in palpable B16 model. GLA is a synthetic hexa-acylated molecule that was shown to have stronger TLR4 agonist than the monophosphyl lipid A, which is currently undergoing clinical trials as a TLR4 agonist adjuvant in cancer vaccines. R848 is a TLR7/8 agonist that was found to produce 50-100 fold cytokines response compared to imiquimod (TLR7 agonist), and this agent has also passed phase 1 trials for safety in patients. We combined these adjuvants that have been tested in patients to be clinically safe individually to formulate TLR Agonist Enhanced GVAX (TEGVAX), and examined their potential to activate APC and to increase the anti-tumor T-cells in the context of established tumors.

Both Li et. al. and Curran et. al. showed that anti-PD-1 and cellular vaccines can be combined to induce an anti-tumor response in vivo, but this report utilized a non-palpable tumor inoculation method which may not model clinical scenarios with established tumor tissue. Curran et. al. also combined anti-CTLA-4 with anti-PD-1 and vaccine, but we chose anti-PD-1 blockade due to the toxicity associated with ipilimumab in both preclinical and clinical studies. With our focus on developing safe vaccines that can generate significant interferon responses in the tumor microenvironment, we utilized a stringent model to test the combinatorial therapy of TEGVAX and anti-PD-1 on palpable, established B16 tumors.

Example 1

Material and Methods

Mice and Reagents: 6-8 weeks old female C57BL/6, Balb/c, and C3H/HeOUJ mice (Jackson Lab) were housed according to the Johns Hopkins Hospital (JHH) Animal Care and Use Committee. C57BL/6 MyD88$^{-/-}$, and B6 (Cg) Rag2tml (Rag2$^{-/-}$) mice were obtained from Drs. Franck Housseau and Fan Pan, respectively (JHH). B16 and B16 GVAX cells were cultured in RPM:14640 media containing 10% ΔFCS, penicillin (100 U/ml) and streptomycin (100 U/ml). The Cytofix/Cytoperm reagent kit and antibodies were purchased from BD Bioscience. CD11c+ cells were isolated by anti-mouse CD11c microBeads (MACS, Miltenyi Biotec). CD4 depleting GK1.5 antibody and CD8 depleting 2.43 (Biox Cell) at 200 μg/dose, were injected intraperitoneally every 2 days (total 5 times). Hybridoma expressing blocking anti-PD-1 antibody (clone G4) was obtained from Dr. Charles Drake (JHH).

Glucopyranosyl lipid A (GLA) at 1 mg/ml and resiquimod (R848) at 0.2 mg/ml resiquimod were prepared in 10% (w/v) squalene oil-in-water emulsion (Immune Design). IDC-1005 is the mixture of 1 mg/ml. GLA and 0.2 mg/ml R848 in emulsion vehicle. IDC-1005 was incubated with irradiated GVAX cells at 4 deg C. for 0.5-2, hours prior to inoculation. GVAX formulated with IDC-1005 is labeled as TEGVAX. In some cases, GLA and R848 without emulsion vehicles were absorbed into GVAX cells with Lipofectamine and washed 4 times to remove non-absorbed TLR agonists and transfectants.

Tumor treatment assay: C57BL/6 mice were injected with 1-5×10$^4$ B16 in the footpads. Once palpable tumor developed (5-10 days), 100 μl of 10$^6$ B16 GVAX formulated with or without IDC-1005 were injected subcutaneously into the contralateral limb. The control groups were injected with vehicle. For all these experiments, 10 mice were used per group. C3H/HeOUJ mice and Balb/c mice were used with SCCFVII/SF cells and CT26 cells, respectively with comparable methods (28). Previously prepared irradiated 10$^6$ SCCFVII/SF-GVAX was used for SCCFVII model in a same manner as B16 (3). For CT26 model, CT26 cells transduced with GM-CSF were used as CT26 GVAX (11). For all the vaccines, GM-CSF was titered to ensure that GM-CSF expression level ranged from 50-500 ng/10$^6$ Cells/24 hours. Tumor was measured daily. In some cases, GVAX were labeled with Qtracker 655 (Invitrogen) prior to inoculation. For the PD-1 experiments, 100 μg/mice/injection was injected intraperitoneally twice a week once tumor was palpable in conjunction with vaccine treatments.

DC activation assay: Spleens and draining lymph nodes (DLN) from tumor-bearing or naive mice were harvested 3-7 days post-vaccine treatments. Crushed spleens were digested in media containing DNAse I (Roche) and Liberase Blendzyme 2 (20,000 Mandl U/ml) (Roche). DC-enriched populations were obtained by depleting CD3 and CD19$^+$, and gated for CD11c$^+$ and B220$^+$. These were evaluated by a multicolored FACS analysis using CD80, CD86, CD40, and MHCII antibodies.

ELISPOT assay: ELISPOT plates (MultiScreen$_{HTS}$ filter plate, Millipore) were coated with a mouse IFN-γ Ab (MabTech) for 24 hours and T2 kb cells were pulsed with 10 μg/ml of P15E (KSPWFTTL) peptide overnight. 10$^6$ splenic CD8 cells from spleen were plated in triplicates to be co-cultured with pulsed or unpulsed 10$^5$ T2 kb cells or stimulated with 1 μM of PMA and 10 ng/ml of Ionomycin as positive controls. On day 3, biotinylated anti-mouse. IFN-γ Ab (MabTeCh) and Strepavidin-HRP were added. AEC Substrate Reagent (BD) was used to develop spots and analyzed using ELISPOT Plate Reader (Immunospot). Zone Name: A1,AMD In vivo CTL assay: Splenocytes were labeled with 0.5 μM and 5μM CFSE (Molecular Probes). The 5 μM CFSE labeled cells were pulsed with 10 μg/ml P15E (KSPWFTTL; SEQ ID NO: 1) peptide. The 0.5 μM CFSE labeled cells pulsed with β-gal (TPHPARIGL; SEQ ID NO: 2) peptide. Mice were injected intravenously with a 1:1 mixture of these cells, and splenocytes were isolated after 24 hours and analyzed by flow cytometry. Antigen-specific killing was calculated using the following formula: (1-% of CFSE$_{p15E}$/% of CFSE $_{β-gal}$) X 100.

Immunohistochemistry: 10 μm thick frozen sections were fixed with acetone, and blocked with 1% BSA for 30 minutes at RT. For paraffin embedded tissue, the sections were fixed in 4% paraformaldehyde prior to 1% BSA blocking as note above. αCD4, αCD8, αCD86 FITC conjugates and αCD45 and αB7-H1 primary antibodies were incubated 1 hour and 4° C. Cy3 conjugate antibody was used as secondary antibody in some cases. DAPI was used as the nuclear counterstain. Positive cells in 10 randomly selected fields at ×40 magnification were quantitated. Quantitation of positive staining was blindly performed (LH) after the IHC slides were stained and marked randomly (JF). The microscope was Nikon, Eclipse E800. The camera was Nikon, DS-Qi1Mc. The software was NIS-Element AR 3.0.

Cytokines analysis: Harvested DC was cultured with Golgistop™ (BD) protein transport monensin and LPS 0.1 μg/ml 5 hrs. DC was stained for anti-mouse CD11c, CD86, MHCII, IL-12, IFNα and TNFα expression, and harvested lymphocytes were stained for anti-mouse IL-2, IFNα, IFNγ, TNFα expression after membrane permeabilization with Cytokit. Data were acquired by FACS analysis after rinsing out the antibodies.

Example 2

Multiple TLR Agonists Enhanced GVAX (TEGVAX) Increased Both Activated Conventional and Plasmacytoid Dendritic Cells in the Draining Lymph Nodes in Comparison to GVAX To further increase the anti-tumor response generated by GVAX, we combined GLA and R848 with GVAX, and tested whether this TEGVAX formulation would increase the number of activated dendritic cells in the DLN of non-tumor bearing mice. Compared to GVAX, TEGVAX was able to enhance the activation phenotype of dendritic cells from the DLN of the vaccine inoculation site (FIG. 1). Both plasmacytoid DCs (pDC) and the conventional DCs (cDC) were analyzed, and both population showed enhanced expression of CD80 and CD86 activation markers for the TEGVAX treated group (FIG. 1A-C). Gated. DCs showed increased activation markers peaking on day 3 after adjuvant injection and this persisted until day 7 (FIG. 1D). Lastly, to assess whether these activated DC provide the appropriate cytokine milieu for an anti-tumor response, cytokine profiles from CD 11c+ cells from the draining lymph nodes also demonstrated increase amount of IL-12, IFNα, and TNFα that can skew the T-cell repertoire towards $T_H1$ response (Supplemental FIG. 1).

Example 3

TEGVAX Treatment of Established Tumors Significantly Reduced Tumor Growth Rate in Vivo We initially tested our TEGVAX with established B16 tumors in a therapeutic model. When the inoculated B 16 tumor was palpable (typically on day 7-10), we treated the tumor bearing mice subcutaneously with TEGVAX, GVAX, GLA/R848 (IDC-1005), and vehicle controls in the contralateral limb. As shown in FIG. 2A, mice that received TEGVAX displayed significantly lower tumor growth rate with only a single treatment. Both GVAX alone and TLR agonists alone had some modest benefit, but the combination treatment produced the best in vivo anti-tumor response. When we compared TEGVAX with GVAX formulation with GLA alone or with R848 alone, we found that the combined GLA/R848 formulation into GVAX had the best anti-tumor response (Supplemental FIG. 2A).

To further improve the anti-tumor response, we performed the experiment with multiple TEGVAX treatments, and found that multiple TEGVAX treated mice did not display the exponential growth seen in untreated mice (FIG. 2B). TEGVAX was injected every 7 days because of the decreased level of activated DC at this point (FIG. 1D). These TEGVAX treated mice with smoldering tumors were inoculated with $10^5$ B16 cells at a different site from the primary tumor site, and, in these mice, no tumor grew at the second site, demonstrating in vivo immunity against subsequent B16 challenges (data not shown). We also tested TEGVAX in the SCCFVII squamous cell carcinoma model in OH mice as well as CT26 colon carcinoma model in Balb/c mice with comparable results, demonstrating that this anti-tumor response applies to multiple tumor histologies and is not dependent on murine background (FIG. 2C) (Supplemental FIG. 3). For the SCCFVII model, single TEGVAX treatment actually induced complete regression of the tumor. Once again, a rechallenge with SCCFVII tumor cells in these mice showed no evidence of tumor growth at the secondary site.

The anti-tumor effect of TEGVAX was dependent on the formulation of the TEGVAX. When we treated the tumor bearing mice with GVAX and GLA/R848 without 1 hour of co-incubation prior to injection, no anti-tumor effect was noted (FIG. 2D). We believe that the co-incubation time can allow the hydrophobic TLR agonists to be absorbed into the GVAX with the squalene oil emulsion vehicle, and that this formulation is necessary for the anti-tumor response of TEGVAX. To test this, we absorbed GLA and R848 into GVAX with. Lipofectamine and washed the cells to remove non-absorbed adjuvants/transfectant, and we found that TEGVAX generated from transfection method is comparable to the TEGVAX generated from prolonged incubation method with lipophilic vehicle in terms of their anti-tumor efficacy (Supplemental FIG. 4).

Example 4

TEGVAX Increased Lymphocytic Infiltration in the Tumor Microenvironment, and this was Associated with Induction of Tumor Necrosis, Locoregional $T_H1$ Response, and Increased B7-H1 Expression on the Tumor We examined the tumor tissue harvested at the completion of our treatment assays, and examined the tumor microenvironment for lymphocytes. Histological analysis showed significantly increased regions of focal necrosis in those mice treated with TEGVAX in comparison to those treated with GVAX or controls (FIG. 3A,B). Immunohistochemistry with CD4 and CD8 antibodies showed that TEGVAX treated tumor had abundant infiltrating CD4 and CD8 cells within the tumor tissue (FIG. 3C,D). When we examined the tumor draining lymph nodes, we noted that TEGVAX treated mice had increased IFNγ+ CD4 and CDR in comparison to GVAX or control treatments. To test whether these increased $T_H1$ cells is associated with the upregulation of B7-H1 on the tumor cells, we stained the tumor tissue and found that TEGVAX also significantly increased the expression of B7-H1 in comparison to GVAX and vehicle treated mice (FIG. 4C).

Example 5

TEGVAX's Anti-Tumor Response was Dependent on Both CD4 and CD8 Cells, as Well as MyD88/TRIF Signaling In order to assess whether T-cells were important for TEGVAX's anti-tumor response, we performed vaccine treatment assays with CD4 and CD8 depletions. TEGVAX treatment effects were abrogated upon depletion of either CD4 or CD8 T-cells, demonstrating the importance of both CD4 and CD8 lymphocytes for the anti-tumor immune response. Experiments using Rag2 KO mice confirmed these findings (FIG. 5A, B, C).

Since multiple TLR agonists were used as the formulation component for TEGVAX, we sought to determine whether TLR signaling was critical for the vaccine effect. TEGVAX treatments of B16 tumor-bearing mice were performed with MyD88/TRIF double knockout mice. Once again, the anti-tumor effect of TEGVAX was completely abrogated in these mice, confirming that TEGVAX's antitumor effect is dependent on TLR signaling (FIG. 5D).

Example 6

TEGVAX Increases the Number of Tumor Specific p15E Specific Cytotoxic T-Cells

Figure 6:
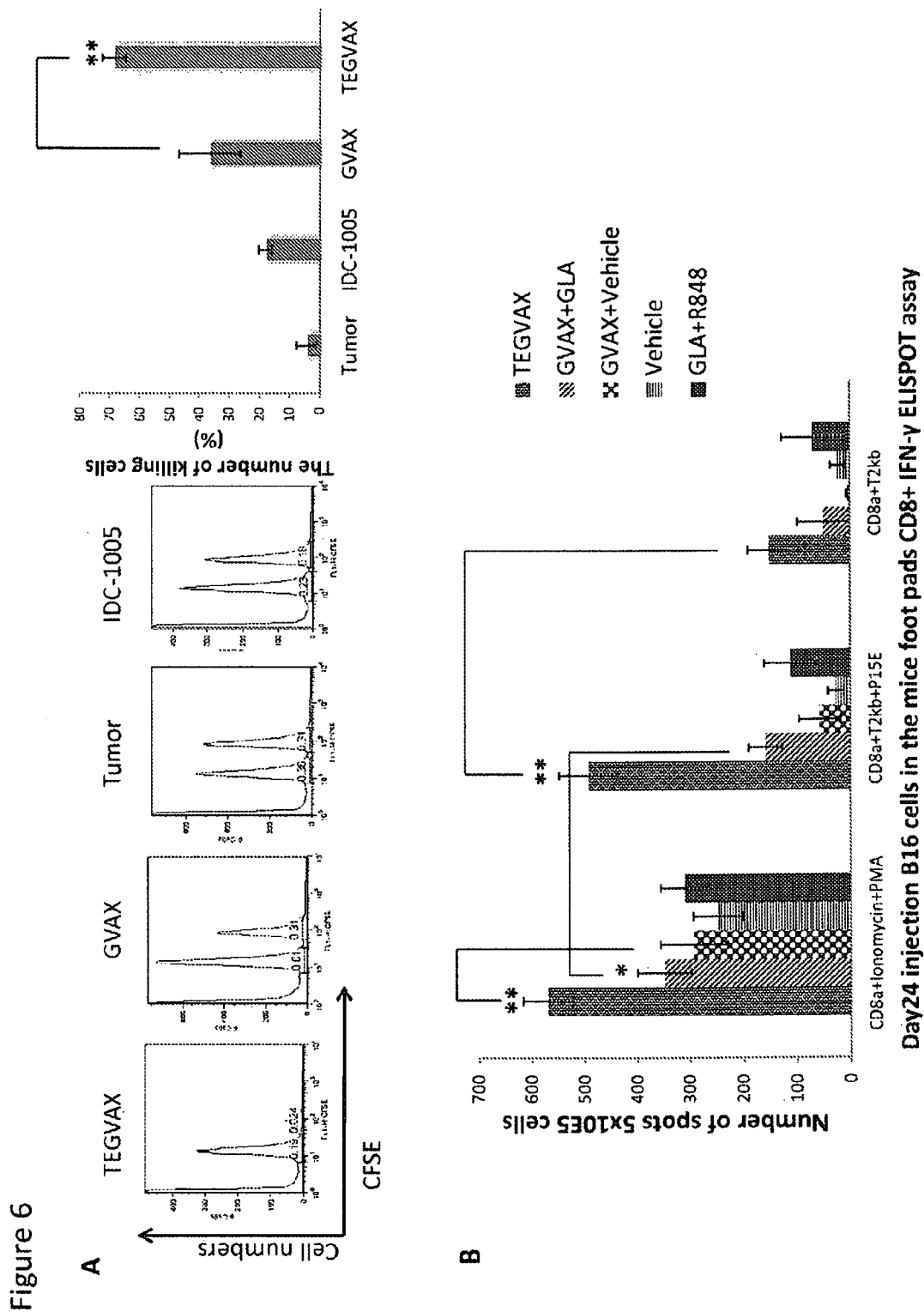
FIG. 6A-B. TEGVAX treated mice has increased number of tumor specific CTL cells. In viva CTL and ELISPOT assay with P15E peptides were performed in B16 tumor bearing mice treated with vaccines and adjuvants.

With clear in vivo evidence of anti-tumor effect with TEGVAX that correlated with activated DC, we also examined the effector arm of immune system. Based on the expression of the immunodominant p15E antigen in B16 tumors, we performed in vivo CTL assay to quantitate the level of p15E specific IFNγ secreting CTLs (FIG. 6). As shown in FIG. 6, at day 21 when there were clear separations in the growth rates of TEGVAX treatment group to the other control groups (FIG. 1), there was increased killing activity of p15E specific CTL in the spleen of the mice treated with TEGVAX in comparison to GVAX or other control mice (FIG. 6A). ELISPOT assays were also performed from CD8 T-cells from each of the treated and control groups with T2 kb cells pulsed with p15E peptide as the APC. These two independent assays demonstrated increased numbers and activity of tumor specific (anti-p15E) CTLs in the mice treated with TEGVAX (FIG. 6B).

Example 7

Figure 4:
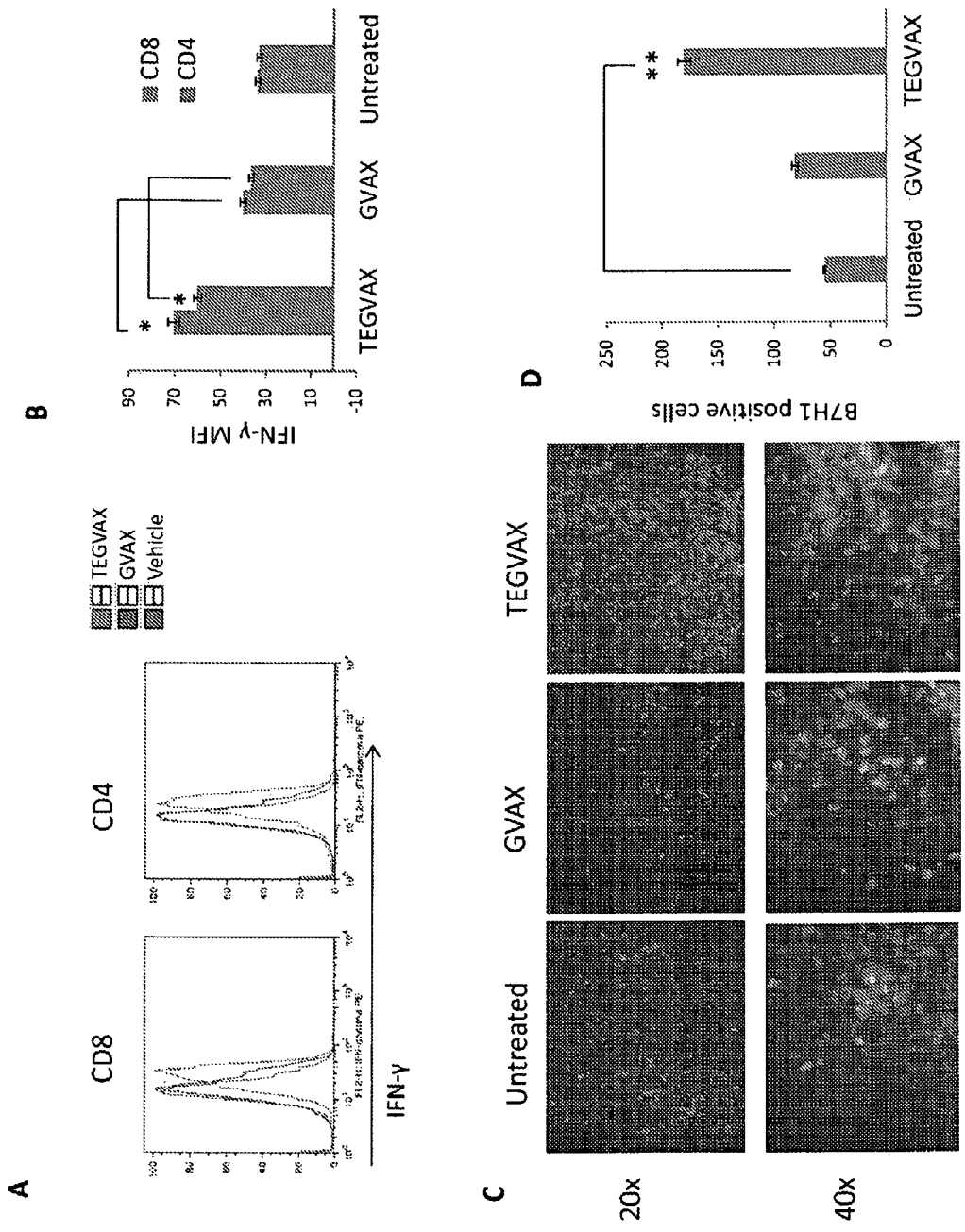
FIG. 4A-4D. TEGVAX induces $T_H1$ response as well as upregulation of B7-H1 expression in the tumor.

TEGVAX Combined with Anti-PD-1 Antibody can Induce Regression of Established B16 Tumor Because of TEGVAX's ability to increase the number of p15E-specific cytotoxic T-cells as well as IFNγ producing CD8 cells, we combined TEGVAX with the blockade of immune checkpoint pathway B7-H1/PD-1. PD-1 is expressed on activated T-cells and the co-localization of its ligand B7-H1, which is upregulated with IFNγ secreting T-cells, on the tumor cells is correlated with clinical efficacy of anti-PD-1 blockade. The implication of these findings that supported the adaptive immune resistance mechanism is that anti-PD-1 blockade is ideally suited to be combined with a vaccine that can generate a powerful $T_H1$ response. In our murine model, TEGVAX increased the both IFNγ secreting T-cells as wells as upregulated the expression of B7-H1 on the tumor cells (FIG. 4). When the anti-PD-1 antibody treatment was combined with TEGVAX, established B16 tumors were noted to regress in 50% of the mice treated (FIG. 7A). In these mice that responded with the combined treatment, vitiligo was noted as shown in FIG. 7B. Mice treated with anti-PD-1 alone or with GVAX had no improvement in tumor growth rate over GVAX treatment alone. These in vivo tumor treatment assays correlated with synergistic effects of increasing $T_H1$ cytokines harvested from the tumor DLN from mice treated with TEGVAX and anti-PD-1 in comparison to the TEGVAX or anti-PD-1 alone. (FIG. 7C).

Example 8

Discussion

Figure 2:
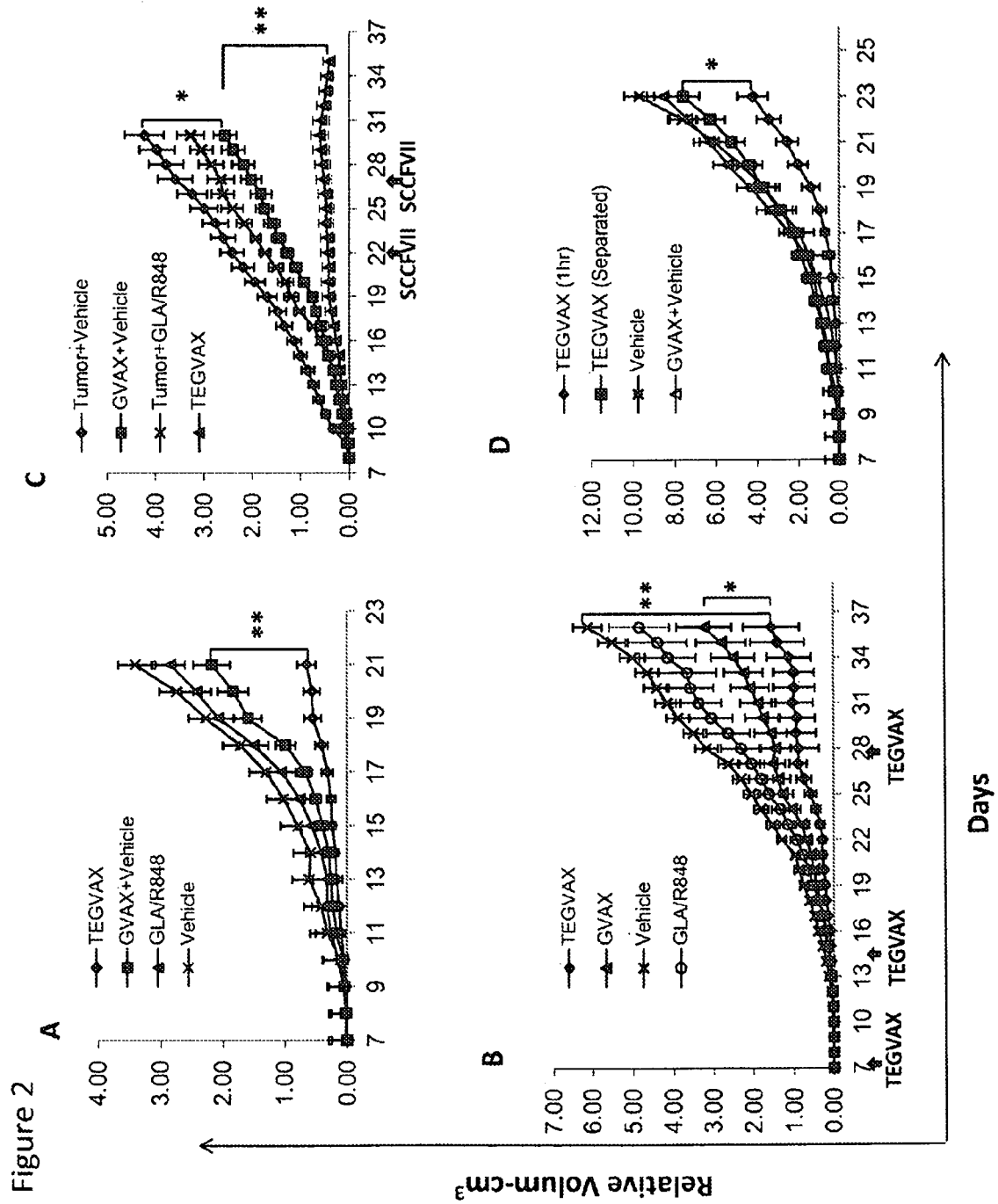
FIG. 2A-2D. TEGVAX induces significant in vivo anti-tumor response in comparison to GVAX in: multiple animal models. All these in vivo treatment experiments are representative of at least 3 separate experiments, and each group in all experiments consists of 10 mice/group.
Figure 3:
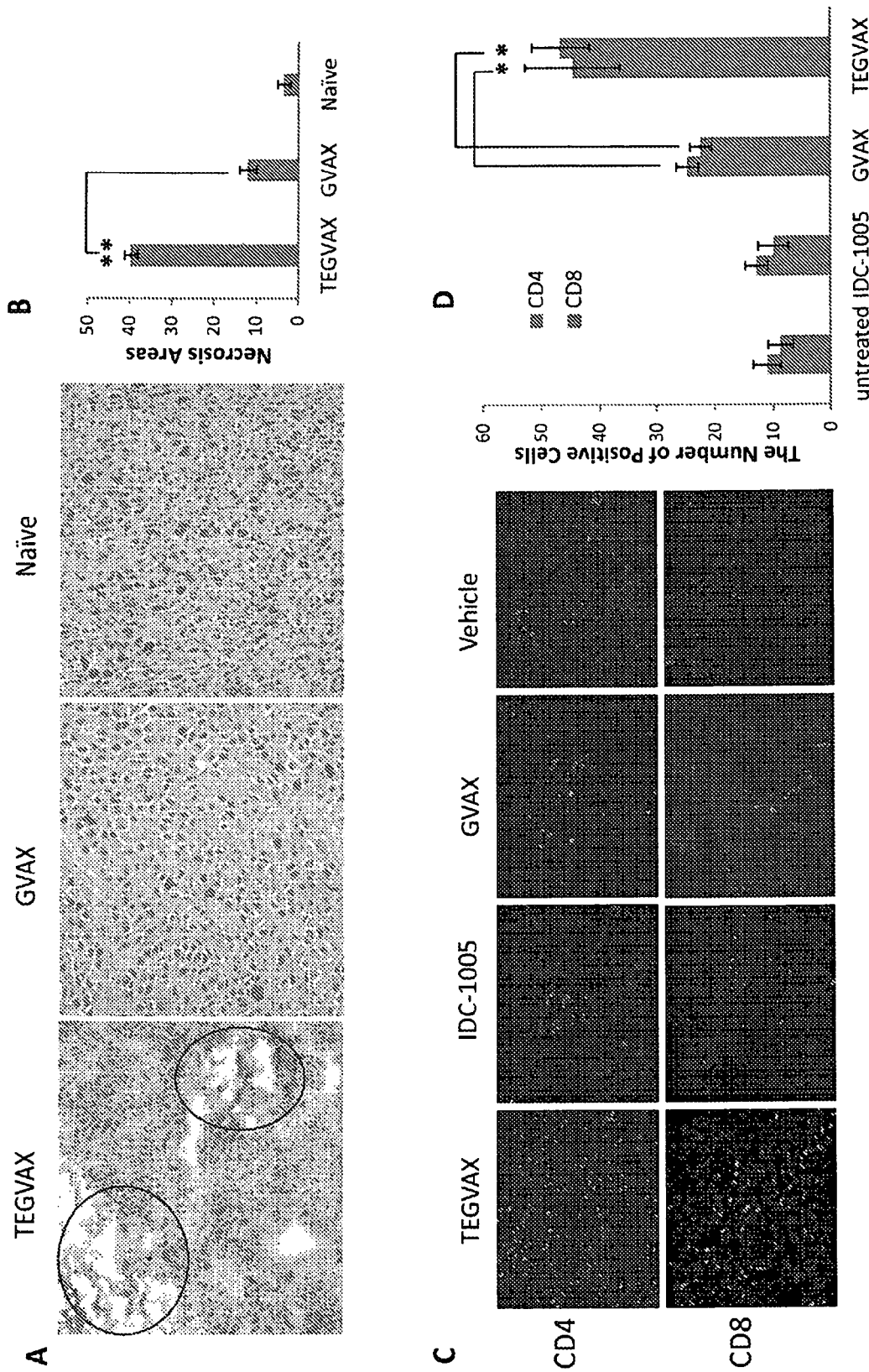
FIG. 3A-3D. TEGVAX treatment increased tumor necrosis and tumor infiltrating lymphocytes and APC.
Figure 7:
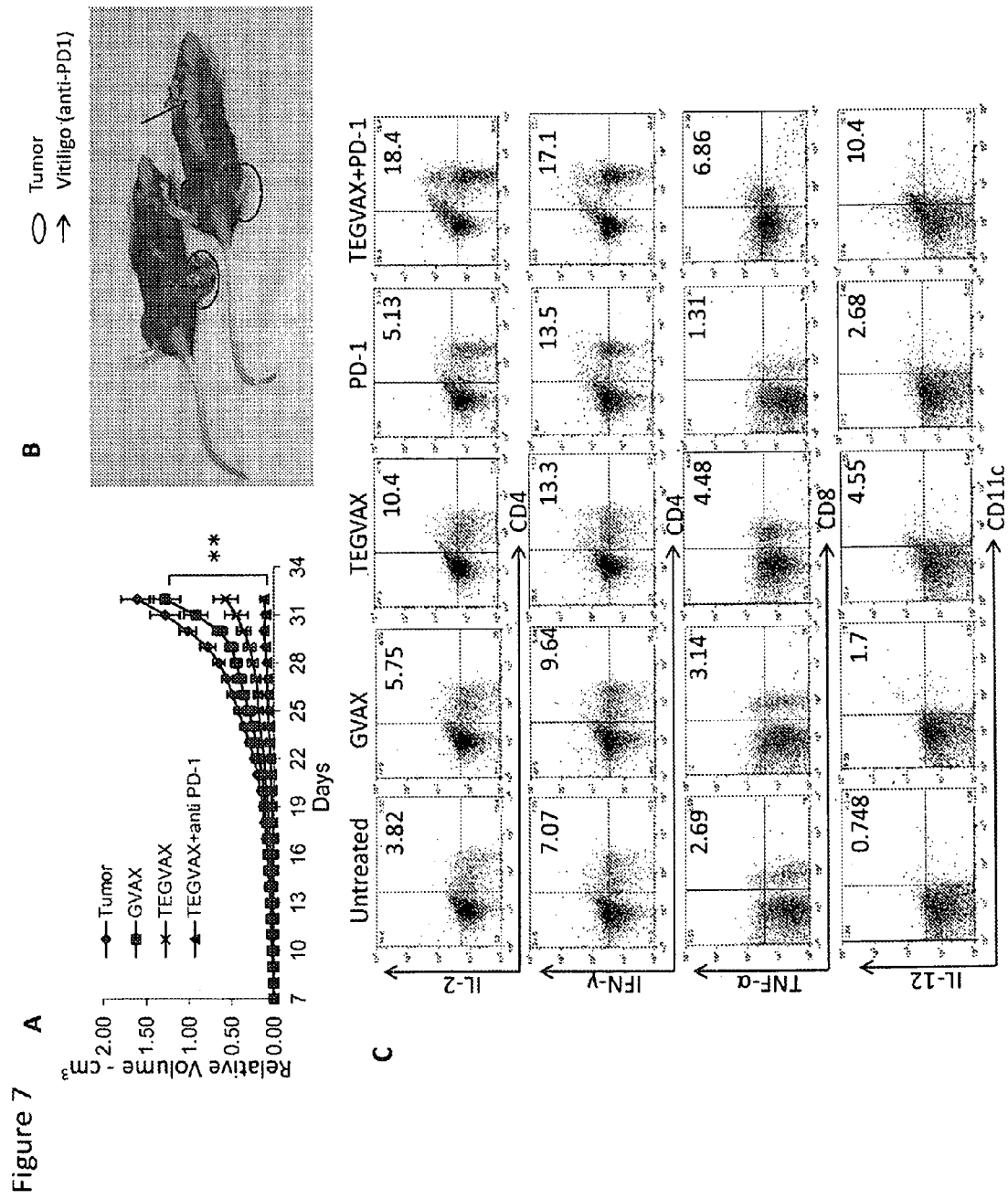
FIG. 7A-7C. TEGVAX/anti-PD-1 treatment can induce regression of established B16 tumors.

In this report, we formulated GVAX with TLR4 (GLA) and TLR7/8 (R848) agonists and demonstrated significant augmentation of in vivo anti-tumor response in comparison to GVAX alone or TLR agonists alone in 3 different murine models. We showed that these adjuvants increased the number of activated plasmacytoid DC (pDC) as well as conventional DC (cDC). These in vivo anti-tumor responses were T-cell dependent, and tumor specific p15E specific T-cells in the B16 model were elevated in the TEGVAX treated group in comparison to GVAX treated group. For these experiments, we used a therapeutic model on established B16 tumors, a poorly immunogenic tumor that cannot be treated with known formulations of vaccines once they become palpable. With repeated TEGVAX treatments, the tumor tend to display a "smoldering" growth rate as shown in FIG. 2. For SCCFVII model, only a single treatment with TEGVAX induced regression of the palpable tumor. For CT26 colon carcinoma model, TEGVAX treatment on palpable lesions also demonstrated in vivo anti-tumor effects (Suppl FIG. 3). TEGVAX treatment was associated with increased IFNγ+ CD4 and CD8 cells in the tumor draining lymph node as well as increased expression of B7-H1 on the tumor cells. When TEGVAX was combined with anti-PD-1 blockade, we observed regression of established B16 tumors as shown in FIG. 7.

GLA and R848 were initially selected because these adjuvants significantly induced enhanced anti-tumor cytokine profiles compared to other TLR agonists, and both have been tested in patients to be safe. GLA, a TLR4 agonist, was compared to monophosphoryl lipid A (MPL) in it ability to activate murine and human dendritic cells, and GLA was found to be more potent in terms of increasing multiple $T_H1$ type cytokines both in vivo and in vitro. R848, a TLR7/8 agonist, was also found have significant improvements in increasing type I IFN profile over imiquimod. Our in vivo results on established tumors, therefore, demonstrated the high translational potential of TEGVAX as a cancer vaccine. Interestingly, when we examined the tumor microenvironment of the treated mice, we noted increased IFNγ level from CD4 and CD8 cells from tumor draining lymph nodes as well as increased B7-H1 expression from the tumor in TEGVAX treated mice in comparison to GVAX (FIG. 4).

Our preclinical studies, therefore, was an excellent venue to test the combinatorial therapy of vaccine with anti-PD-1 blockade. The importance of B7-H1 induction on tumor cells and its engagement with PD-1 on lymphocytes as a critical immune evasion mechanism was demonstrated in preclinical models, and B7-H1 expression was clinically correlated with worse prognosis in multiple cancer types. For patients with advanced melanoma, lung cancer, and renal carcinoma, monotherapy with blocking anti-PD-1 antibody resulted in significant survival benefit, and concurrent histological analysis demonstrated strong correlation between B7-H1 and IFNγ expression and response to PD-1 blockade In epithelial tissues as well as B16-F10 tumor cells, IFNγ can induce B7-H1 expression. Cumulatively, these findings support the adaptive resistance mechanism whereby anti-PD-1 blockade can unleash its anti-tumor efficacy of resident tumor specific cytotoxic T-cells that induce its own suppression by inducing B7-H1 on the tumor partly via IFNγ. Anti-PD-1 blockade is therefore ideally suited for combinatorial therapy with IFNγ inducing vaccine. The regression of established B16 with TEGVAX/anti-PD-1 treatment shown in FIG. 7 provide in vivo preclinical justification for clinical trial combining anti-PD-1 therapy with an appropriate vaccine.

Previous reports showed that the combination of anti-PD-1, anti-CTLA-4, and vaccine may promote anti-tumor responses, but their in vivo assay involved initiating treatment on non-palpable, nonestablished B16 tumor. Our treatment assay was much more stringent in that we initiated treatment 7-10 days after B16 inoculation, at which point most immunotherapy fail. Moreover, we did not need to combine anti-PD-1 with other immune checkpoint blockade antibodies to demonstrate regression of established tumor.

The synergistic effect of combining TEGVAX and anti-PD-1 was corroborated when we examined the draining lymph nodes from the tumor. Tumor infiltrating lymphocyte (TIL) collection was not feasible because of the regressed tumor or the small tumor size to sample sufficient cells for flow cytometry. However, both CD4 and CD8 lymphocytes and CD11c+ dendritic cells from the popliteal lymph nodes displayed several fold increase in IL-2, IL-12, and IFNγ expression level in comparison to the modest elevation in the TEGVAX or anti-PD-1 treated groups alone (FIG. 7C). These $T_H1$ cytokines correlated with the increased number of p15E specific CTL in the TEGVAX/anti-PD-1 treated group in comparison to the TEGVAX and the PD-1 treated groups (data not shown).

From a translational standpoint, ipilimumab is associated with grade 3-4 toxicity and isolated reports of therapy related mortality, so the addition of anti-CTLA-4 antibody may not be the first option to improve upon our in vivo results. However, because of significant redundancy in the many families of immune checkpoint molecules as well as the availability of clinical grade checkpoint blocking antibodies, there are potentials to add other immune checkpoint blocking antibodies to anti-PD-1 treatment. Because of the likelihood that increased IFNγ can potentially upregulate B7-H1 in the tumor microenvironment, an alternative approach would be to increase the level of tumor specific CTLs using a safe vaccine that can be combined with anti-PD-1. For the purpose of this study, we chose two TLR agonists with TLR4 and TLR7/8 activity, but it is unclear whether other TLR agonists (flagellin, CpG, etc) or other PAMP molecules can further augment the anti-tumor response. Lastly, it should be reiterated that all the components of TEGVAX have been tested in patients to be safe. With its demonstration as a potent anti-tumor agent by itself, TEGVAX in combination with anti-PD-1 antibody has high translational potential for clinical trials.

We previously demonstrated an in vivo response with intratumoral injection using GVAX formulated with LPS, but now we report a much more potent response with GVAX formulated with both. TLR4 and TLR7/8 agonist as a therapeutic. The mechanisms that underlie the intratumoral injection in comparison to the systemic injection in these treatment models are different, but cumulatively, these experiments demonstrate that TLR agonists formulated with a cellular vaccine injected intratumorally or systemically will unlikely have a pro-carcinogenic effect. MyD88-NF-κB signaling pathways in tumor cells have been shown to have pro-carcinogenic consequences. However, TLR agonists have been clearly shown to activate MyD88-TRIF pathways in dendritic cells to prime the adaptive immune system for anti-tumor responses. In this report, the TLR agonists formulated into GVAX can stimulate the DC in the draining lymph nodes, and any untoward pro-carcinogenic effects could not be demonstrated in our systemic treatment models.

GVAX, and in some models, the TLR agonists themselves, has an early modest effect in the tumor growth rate, but there is clear separation between the TEGVAX group and control groups in all the murine models studied. We also compared GLA/GVAX and R848/GVAX against TEGVAX, and it is clearly TEGVAX that combines both TLR4 and TLR7/8 activities that has the best in vivo anti-tumor response (Supplemental FIG. 2). For B16 experiments, viable B16 tumor cells were injected subcutaneously distant from the site of initial tumor inoculation or vaccine inoculation, and no tumor growth were noted. Similarly for SCCFVII model, a rechallenged experiment showed no outgrowth of tumor after only a single TEGVAX treatment (FIG. 2C).

Figure 5:
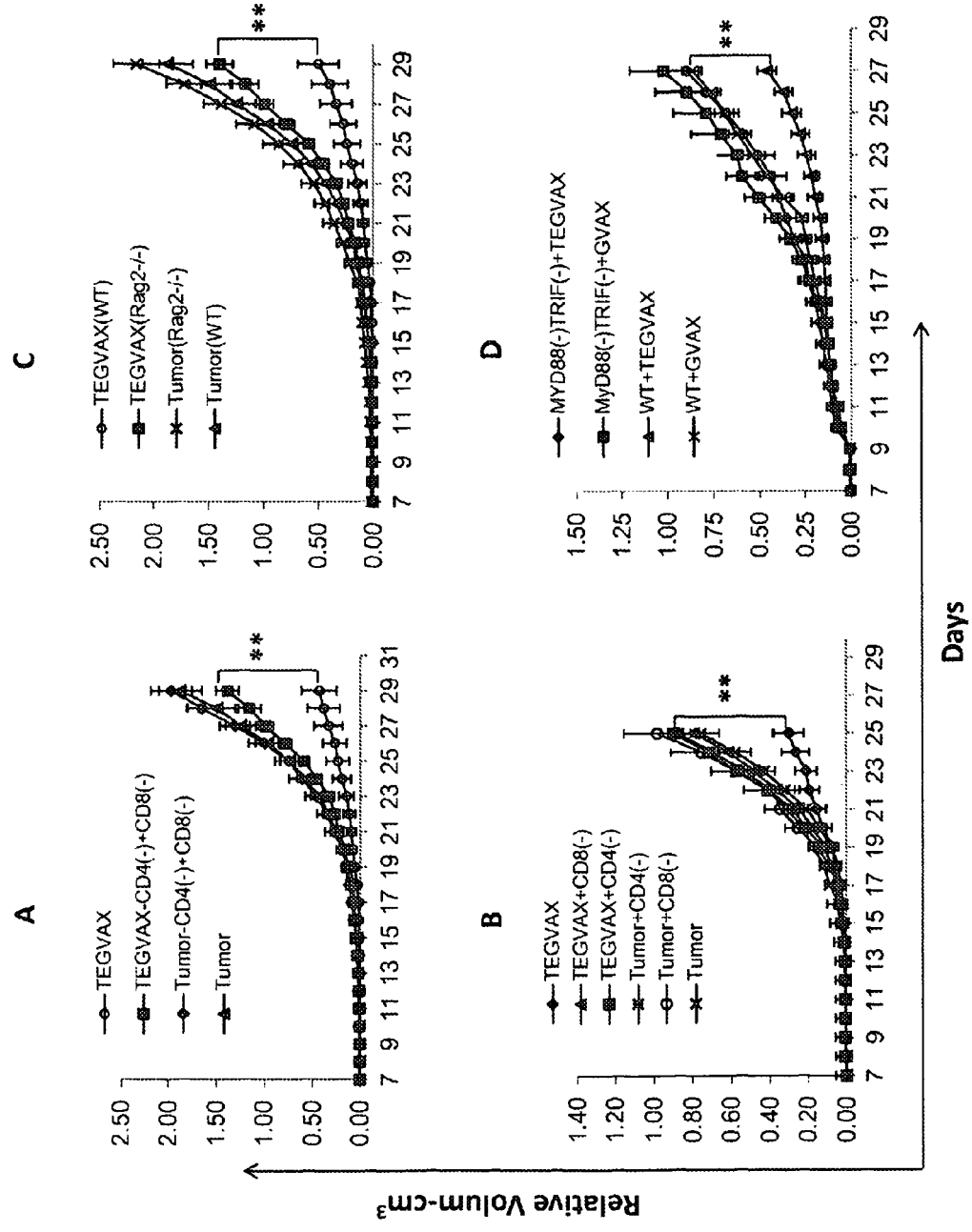
FIG. 5A-5D. The in viva anti-tumor response of TEGVAX is both CD4 and CD8 T-cell dependent.

We feel that it is the combination of both TLR4 and TLR7/8 stimulation that can increase both cDC as well as pDC to induce robust priming of T-cells into anti-tumor T-cells that is responsible for the in vivo anti-tumor effect of TEGVAX. TEGVAX treatment assay was performed with MyD88-TRIF double knockout mice, and the anti-tumor effect was completely abrogated (FIG. 4C). MyD88 is the critical mediator for TLR7/8 signaling, and both TRIF and MyD88 is the critical downstream mediator of TLR4 signaling. When we examined the draining lymph node CD11c+ cells, we noted increase $T_H1$ cytokines expression for TEGVAX treated group in comparison to controls (FIG. 5). Dot plot of CD11c and these $T_H1$ cytokines were informative in that the increase in the double positives are derived predominantly from the shift in the CD11c+ population, suggesting that the addition of TLR agonists primarily induced increased trafficking of APCs to the lymph nodes rather than increase the production of inflammatory cytokines on a per cell basis. To this end, we labeled TEGVAX with Q-dot, and quantitated the endogenous APC's that was labeled via cell-to-cell transfer with Q-dot in the draining lymph node (Supplemental FIG. 5). For both pDC and cDC population, there were quantitatively more activated DCs that were labeled with Q-dot, consistent with our hypothesis that the TLR adjuvants increase the number of activated DC that circulate between the tumor and the draining lymph nodes where they can prime the T-cells.

Our previous work with LPS absorbed GVAX demonstrated that the absorption of TLR4 agonist into a cellular vaccine was critical for in vivo anti-tumor efficacy. We surmised that the absorption of GLA and 848 into GVAX is also critical for the enhanced anti-tumor response observed with TEGVAX. When we simply co-inject the GLA and R848 adjuvants with GVAX without any incubation, there was no in vivo anti-tumor response (FIG. 2D). Only when the TLR agonists and GVAX are incubated with lipophilic vehicles for an hour did we obtain a TEGVAX formulation that was able to induce a partial response for the B16 model as well as induce regression for the SCCFVII model. To further test this, we formulated GVAX with GLA and 848 using Lipofectamine without squalene oil-in-water emulsion, and demonstrated comparable in vivo anti-tumor response in the B16 model (Supplemental FIG. 4). One aspect of the future work, therefore, involves further optimization of TEGVAX formulation.

Cumulatively, this report demonstrates that TEGVAX offers a significant improvement over GVAX as a therapeutic vaccine that can significantly augment the priming of tumor specific T-cells, even for established tumors, and it is an excellent candidate to be added in a combinatorial therapy with anti-PD-1 blocking antibody or other forms of immune checkpoint blockade in cancer patients.

The invention claimed is:

1. A composition comprising:
cytokine-expressing, proliferation incompetent, whole cancer cells;
an anti-PD-1 antibody that specifically binds to human Programmed Death 1 (PD-1); and
a TLR (toll like receptor) agonist;
wherein the whole cancer cells are formulated with the TLR agonist.

2. The composition of claim 1 wherein the cytokine is GM-CSF (Granulocyte-macrophage colony stimulating factor).

3. The composition of claim 1 wherein the whole cancer cells are autologous to the patient.

4. The composition of claim 1 wherein the whole cancer cells are formulated with a TLR7/8 agonist.

5. The composition of claim 1 wherein the whole cancer cells are formulated with a TLR4 agonist.

6. The composition of claim 1 wherein the whole cancer cells are formulated with a TLR4 and a TLR7/8 agonist.

7. The composition of claim 1 wherein the TLR agonist is selected from the group consisting of GLA, R848, and a combination thereof.

8. The composition of claim 1 wherein the cancer cells are melanoma cells.

9. The composition of claim 1 wherein the TLR agonist and whole tumor cells are formulated with an emulsion vehicle.

10. The composition of claim 1 wherein the TLR agonist and whole tumor cells are formulated with Lipofectamine™.

11. The composition of claim 1 wherein the TLR agonist and whole tumor cells are formulated with a cationic lipid.

12. A method comprising:
administering to a cancer patient immunotherapeutic agents:
cytokine-expressing, proliferation incompetent, whole cancer cells;
an anti-PD-1 antibody that specifically binds to human Programmed Death 1 (PD-1); and
a TLR (toll like receptor) agonist;
wherein the whole cancer cells are formulated with the TLR agonist.

13. The method of claim 12 wherein the cytokine is GM-CSF (Granulocyte-macrophage colony stimulating factor).

14. The method of claim 12 wherein the whole cancer cells are autologous to the patient.

15. The method of claim 12 wherein the whole cancer cells are formulated with a TLR7/8 agonist.

16. The method of claim 12 wherein the whole cancer cells are formulated with a TLR4 agonist.

17. The method of claim 12 wherein the whole cancer cells are formulated with a TLR4 and a TLR7/8 agonist.

18. The method of claim 12 wherein the TLR agonist is selected from the group consisting of GLA, R848, and a combination thereof.

19. The method of claim 12 wherein the whole cancer cells are melanoma cells.

20. The method of claim 12 wherein the TLR agonist and whole tumor cells are formulated with an emulsion vehicle.

21. The method of claim 12 wherein the TLR agonist and whole tumor cells are formulated with Lipofectamine™.

22. The method of claim 12 wherein the TLR agonist and whole tumor cells are formulated with a cationic lipid.

23. A kit comprising agents:
cytokine-expressing, proliferation incompetent, whole cancer cells;
an anti-PD-1 antibody that specifically binds to human Programmed Death 1 (PD-1); and
a TLR (toll like receptor) agonist.

24. The kit of claim 23 further comprising instructions for administering and/or formulating the agents.

25. The kit of claim 23 further comprising an emulsion vehicle.

26. The kit of claim 23 further comprising Lipofectamine™.

27. The kit of claim 23 further comprising a cationic lipid.

* * * * *